(12) United States Patent
Furuya et al.

(10) Patent No.: US 6,646,178 B2
(45) Date of Patent: Nov. 11, 2003

(54) ABSORBENT ARTICLE WITH SURFACE MEMBER OF CONTINUOUS FILAMENTS

(75) Inventors: Kodai Furuya, Kagawa (JP); Hiroo Hayashi, Kagawa (JP); Takamitsu Igaue, Kagawa (JP); Shinya Kaneko, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 83 days.

(21) Appl. No.: 09/934,957

(22) Filed: Aug. 22, 2001

(65) Prior Publication Data

US 2002/0029024 A1 Mar. 7, 2002

(30) Foreign Application Priority Data

Sep. 1, 2000 (JP) ........................................ 2000-265496

(51) Int. Cl.[7] .................................................. A61F 13/15
(52) U.S. Cl. ........................ 604/367; 604/378; 604/384
(58) Field of Search ................................ 604/378, 379, 604/367, 384

(56) References Cited

U.S. PATENT DOCUMENTS

| | | | | |
|---|---|---|---|---|
| 3,949,130 A | * | 4/1976 | Sabee et al. | 428/192 |
| 5,492,751 A | * | 2/1996 | Butt et al. | 428/198 |
| 5,695,487 A | * | 12/1997 | Cohen et al. | 604/384 |
| 5,752,945 A | * | 5/1998 | Mosley et al. | 604/370 |
| 5,997,989 A | * | 12/1999 | Gessner et al. | 428/152 |
| 6,245,961 B1 | * | 6/2001 | Roxendal et al. | 604/367 |
| 6,417,427 B1 | * | 7/2002 | Roxendal et al. | 604/378 |
| 6,488,670 B1 | * | 12/2002 | Schild et al. | 604/385.24 |

FOREIGN PATENT DOCUMENTS

| | | | |
|---|---|---|---|
| JP | 56-141612 | 3/1955 | |
| JP | 57-13609 | 6/1955 | |
| JP | 05-176954 | 7/1993 | ........... A61F/13/54 |
| WO | WO 95/24877 | 9/1995 | ........... A61F/13/15 |

* cited by examiner

*Primary Examiner*—Weilun Lo
*Assistant Examiner*—Jamisue Webb
(74) *Attorney, Agent, or Firm*—Darby & Darby

(57) ABSTRACT

Disclosed is an absorbent article including: a liquid permeable surface member; a backing sheet; and an absorbent layer interposed between the surface member and the backing sheet. The surface member includes an upper layer located at a liquid-receiving side surface and a lower layer located adjacent to the absorbent layer. The upper layer is formed of first continuous filaments. The lower layer is formed of second continuous filaments. The first and second continuous filaments individually extend over the entire length of the surface member. Hydrophilicity of the lower layer is higher than that of the upper layer.

1 Claim, 4 Drawing Sheets

ABSORBENT ARTICLE WITH SURFACE MEMBER OF CONTINUOUS FILAMENTS

BACKGROUND OF THE INVENTION

1. Field of the Invention

The present invention relates to an absorbent article, such as sanitary napkin, disposable diaper or the like, which has a surface member formed of continuous filaments.

2. Description of the Related Art

Absorbent articles, such as sanitary napkins, disposable diapers or the like are generally constructed such that a liquid impermeable backing sheet is stacked on the back side of an absorbent layer, and a liquid permeable surface member is stacked on the surface side as a liquid-receiving side.

As functions of the surface member of the absorbent article, it is required to have superior liquid permeability for permitting liquid to flow toward the absorbent layer, and to achieve high effect in preventing liquid from flowing back. Here, the phenomenon where liquid once absorbed in absorbent layer flows back toward the surface side is often referred to as "rewet".

For example, in Japanese Unexamined Patent Publication No. 5-176954, there is disclosed a surface member, in which a spun bonded non-woven fabric formed of hydrophobic continuous filaments and a thin paper formed of pulp fibers are stacked and the continuous filaments and the pulp fibers are entangled by action of water flow. In this prior art, by contacting the hydrophobic spun bonded non-woven fabric and the hydrophilic thin paper on the entire surface, body fluid is easily absorbed and passed by absorbing force of the pulp fibers forming the thin paper.

However, since this conventional surface member requires a process step of applying water flow, production cost becomes high. Also, since water flow is applied, basis weight becomes high and bulkiness becomes low to lack soft feeling as a surface member.

On the other hand, in Japanese Unexamined Patent Publication No. 9-510374, there is disclosed a surface member in which a first sheet and a second sheet are stacked in spaced apart relationship via a spacer to exhibit capillary effect by a gap defined between the first and second sheets to easily pass the body fluid.

However, since this conventional surface member employs complicate structure for requiring placing two sheets in spaced apart relationship by the spacer, difficulty is encountered in manufacturing and this is less practical.

On the other hand, as other prior art, there is a surface member in which a hydrophilic non-woven fabric is stacked below a hydrophobic non-woven fabric and these two kinds of non-woven fabric are adhered. In this surface member, permeability of body fluid is improved by liquid absorbing ability of the lower hydrophilic non-woven fabric.

However, in this conventional surface member, since the hydrophobic non-woven fabric and the hydrophilic non-woven fabric are adhered with a hot melt type adhesive or the like, the adhesive is inherently present on the interface between the non-woven fabrics to serve to block flow of the liquid.

On the other hand, Japanese Unexamined Utility Model Publication No. 57-13609, Japanese Unexamined Utility Model Publication No. 56-141612 and so forth, disclose absorbent articles, in which a layer of hydrophobic continuous filaments is provided on the surface side of the absorbent layer. In these absorbent articles employing the continuous filament layer as a surface layer, the surface layer has a low filament density and a high bulkiness. Therefore, it can provide soft contact feeling on the skin of a wearer. In addition, since the relatively bulky, hydrophobic filament layer is present between the absorbent layer and the skin of a wearer, flowing back of liquid once absorbed in the absorbent layer (i.e., rewet) can be easily prevented.

However, since the relatively bulky, hydrophobic filament layer is present on the surface of the absorbent layer, body fluid is difficult to penetrate into the absorbent layer to cause a defect that the body fluid may be retained in the filament layer.

SUMMARY OF THE INVENTION

The present invention has been worked out in view of the problem in the prior art set forth above. It is, therefore, an object of the present invention to provide an absorbent article having a surface member which provides soft contact feeling on the skin of a wearer, high liquid permeability and high rewet-preventing property, and which is easy to manufacture.

According to the invention, there is provided an absorbent article comprising:

a liquid permeable surface member;

a backing sheet;

an absorbent layer interposed between the surface member and the backing sheet, and the surface member having at least two layers including an upper layer located at a liquid-receiving side surface and a lower layer located adjacent to the absorbent layer, the upper layer being formed of first continuous filaments, the lower layer being formed of second continuous filaments, the first and second continuous filaments individually extending over the entire length of the surface member, and hydrophilicity of the lower layer being higher than that of the upper layer.

For example, the first and second continuous filaments may be respectively prepared by applying a hydrophilic oil solution on surfaces of hydrophobic filaments, and durability of a hydrophilic oil solution applied to the second continuous filaments may be higher than that of a hydrophilic oil solution applied to the first continuous filaments.

In an alternative, the first and second continuous filaments may be respectively prepared by applying a hydrophilic oil solution on surfaces of hydrophobic filaments, and the application amount of the hydrophilic oil solution to the second continuous filaments may be greater than the application amount of the hydrophilic oil solution to the first continuous filaments.

In another alternative, the first continuous filaments may be hydrophobic filaments and the second continuous filaments may be hydrophilic filaments. In still another alternative, the first continuous filaments may be hydrophobic filaments not treated to be hydrophilic and the second continuous filaments may be hydrophobic filaments treated to be hydrophilic.

Preferably, a density of the first continuous filaments in the upper layer is different from a density of the second continuous filaments in the lower layer. More preferably, a density of the second continuous filaments in the lower layer is higher than a density of the first continuous filaments in the upper layer. In this case, number of crimp in the first continuous filaments and number of crimp in the second continuous filaments may be respectively in a range of 5 to 30 per 1 inch, but may be different from each other so that the difference in density is caused by the difference in number of crimp, and/or crimp modulus of elasticity of the first continuous filaments and crimp modulus of elasticity of the second continuous filaments may be respectively greater than or equal to 70%, but may be different from each other so that the difference in density is caused by the difference in crimp modulus of elasticity.

In the present invention, since the surface member is formed of the continuous filaments to have a low density and a high bulk, it provides soft contact feeling to the skin of a wearer. Especially, since the individual continuous filaments extend over the entire length of the surface member to have no fiber end appearing on the surface, the surface is made so smooth.

Moreover, since a difference in hydrophilicity is provided between the upper layer and the lower layer in the surface member of the continuous filaments, liquid permeability of the surface member is improved and the rewet-preventing effect is enhanced.

Still moreover, the surface member having the layers of different hydrophilicities can be easily manufactured by continuously feeding the continuous filaments of different hydrophilicities and by partially fixing them.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment of the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structure are not shown in detail in order to avoid unnecessary obscurity of the present invention.

Figure 1:
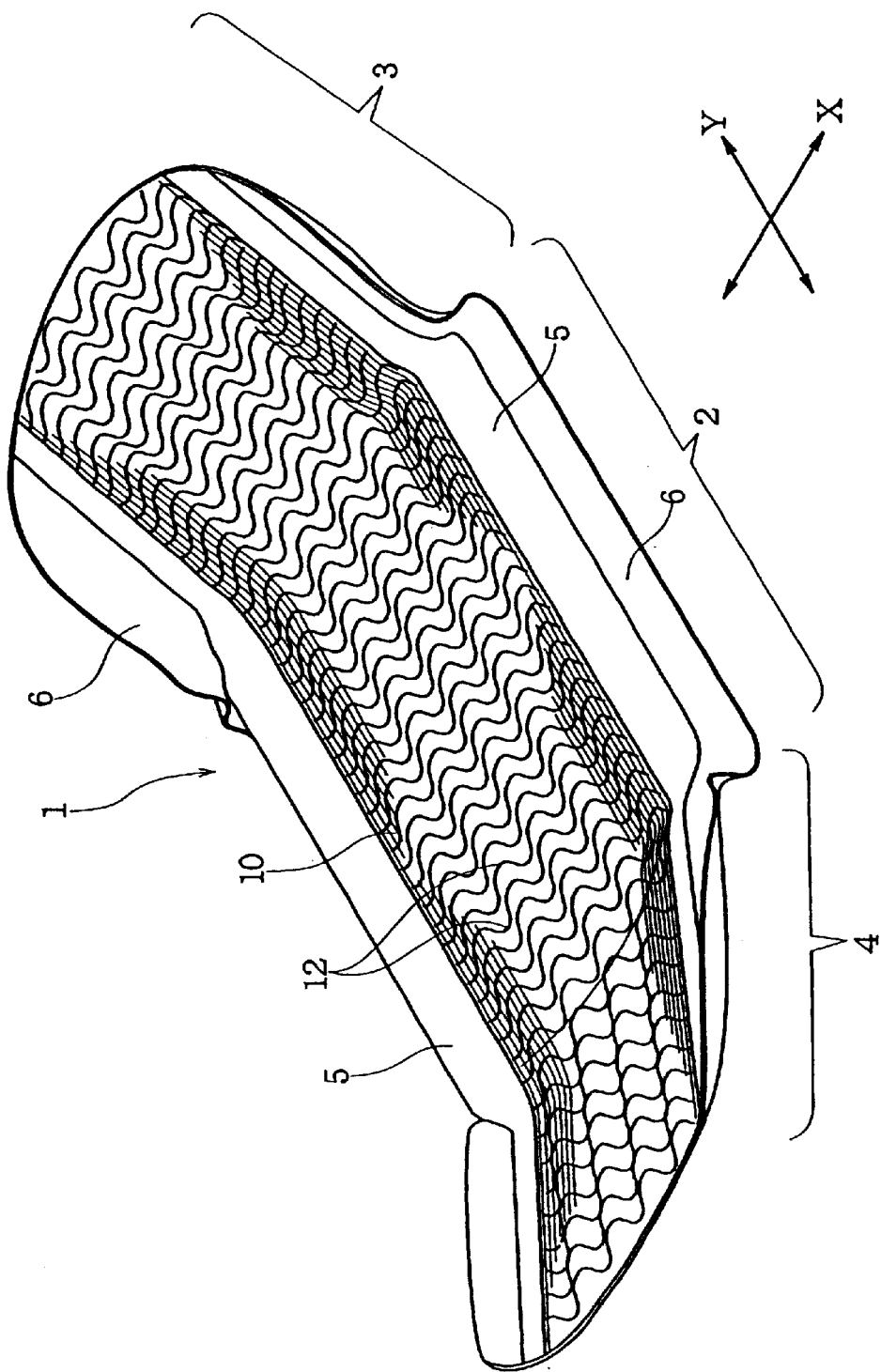
FIG. 1 is a perspective view showing an absorbent article according one embodiment of the present invention.
Figure 2:
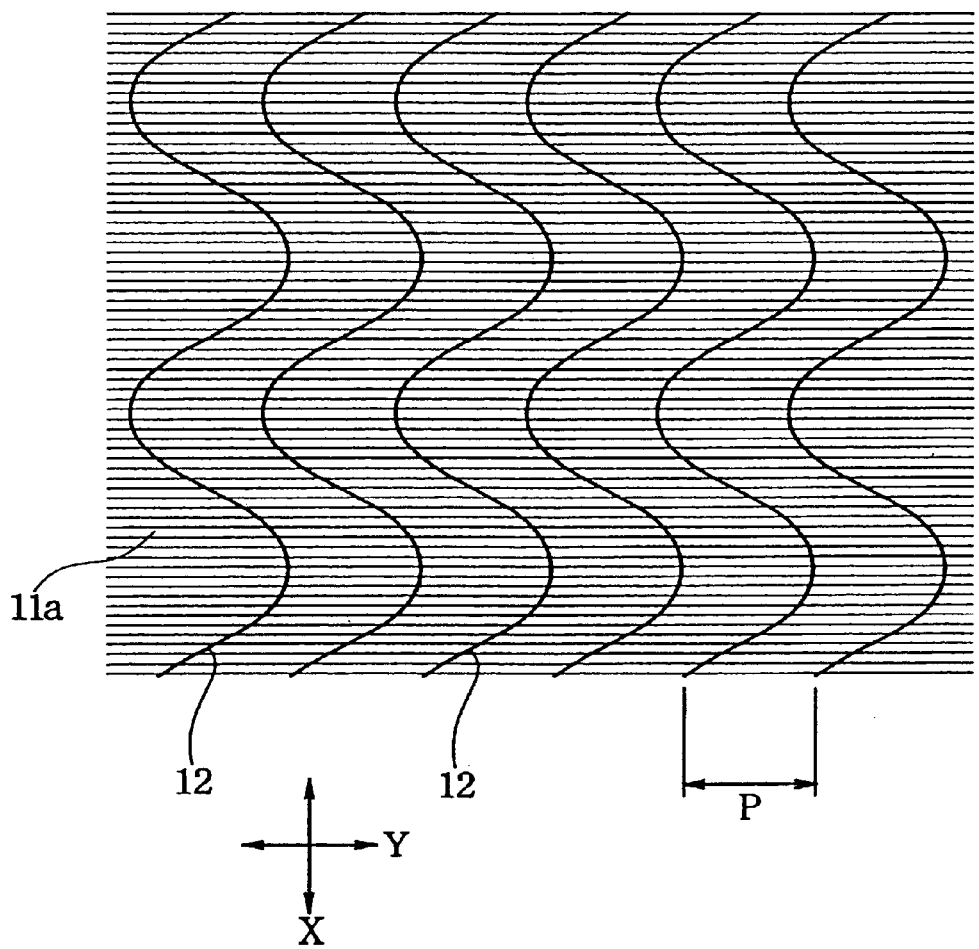
FIG. 2 is a partial plan view of a surface member of the absorbent article shown in FIG. 1.
Figure 3A:
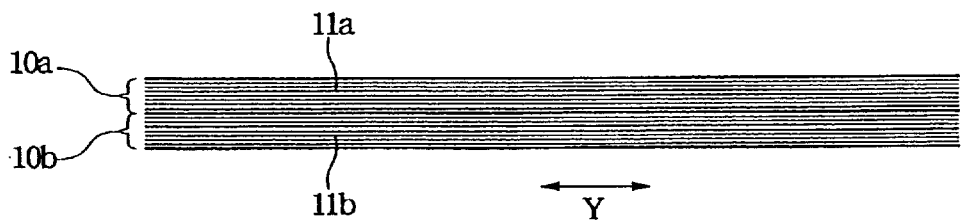
FIG. 3A is a partial section showing a condition where continuous filaments of an upper layer is stacked on continuous filaments of a lower layer.
Figure 3B:
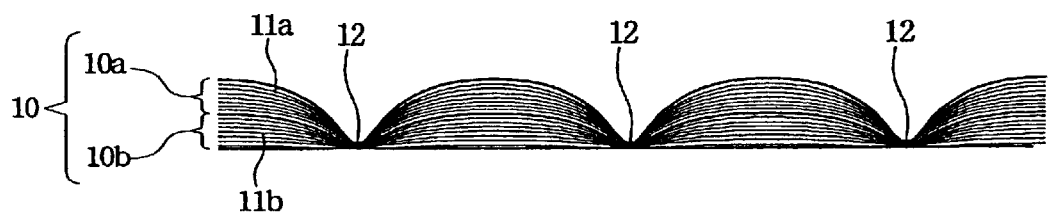
FIG. 3B is a partial section showing a condition where stacked continuous filaments are partially fusion bonded for forming the surface member.
Figure 4:
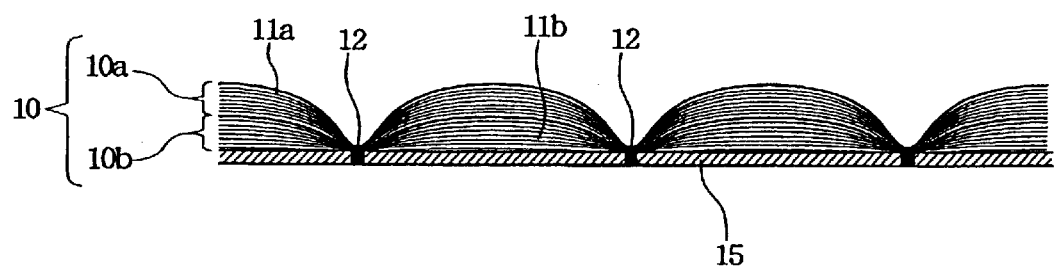
FIG. 4 is a partial section showing a surface member according to another embodiment of the present invention.
Figure 5:
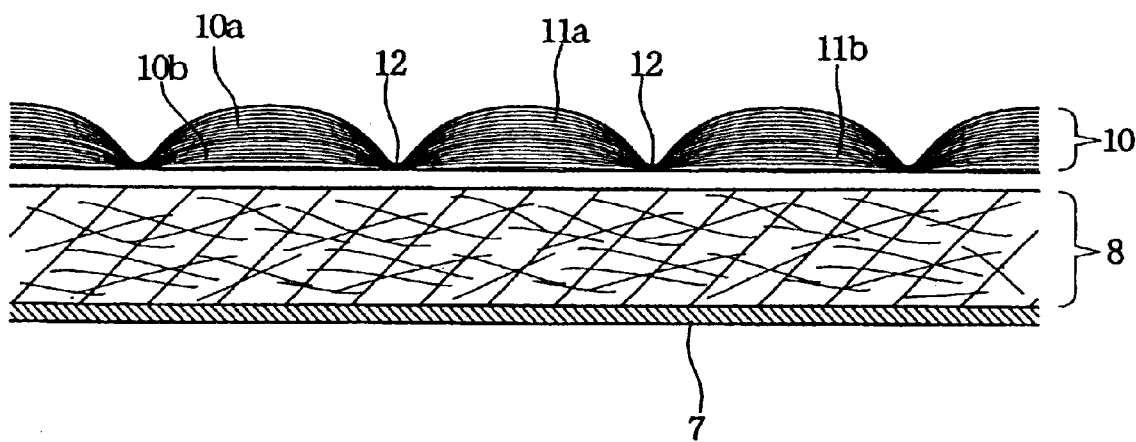
FIG. 5 is a partial section showing the absorbent article and the surface member.

FIG. 1 is a perspective view showing an absorbent article according to one embodiment of the present invention, FIG. 2 is a partial plan view of a surface member of the absorbent article shown in FIG. 1, FIG. 3A is a partial section showing a condition where continuous filaments of an upper layer is stacked on continuous filaments of a lower layer, FIG. 3B is a partial section showing a condition where stacked continuous filaments are partially fusion bonded for forming the surface member, FIG. 4 is a partial section showing a surface member according to another embodiment of the present invention, and FIG. 5 is a partial section showing the absorbent article and the surface member.

An absorbent article 1 shown in FIG. 1 is a sanitary napkin, in which a width direction is defined as X direction and a longitudinal direction is defined as Y direction. The absorbent article 1 has an intermediate portion 2, and front and rear portions 3 and 4 lying opposite one another in the longitudinal direction and having the intermediate portion 2 located therebetween. At two lateral sides of a main body of the absorbent article 1, side leakage preventing walls 5 and 5 extending in the longitudinal direction (Y direction) are provided. To the leakage preventing walls 5 and 5, elastic members for exhibiting elastic contracting force in the longitudinal direction are provided. By the elastic contracting force, the main body of the absorbent article 1 is curved in the longitudinal direction, and the leakage preventing walls 5 and 5 are three-dimensionally raised from the liquid-receiving face of the main body, mainly at the intermediate portion 2.

As shown in the section of FIG. 5, the main body of the absorbent article 1 is constructed to include a liquid impermeable backing sheet 7, an absorbent core (absorbent layer) 8 stacked on the backing sheet 7, and a liquid permeable surface member 10 stacked over the absorbent core 8. The surface member 10 is formed of at least two kinds of continuous filaments having different hydrophilicities.

The absorbent core 8 is provided from the intermediate portion 2 to part of the front and rear portions 3 and 4. The surface member 10 is provided between the leakage preventing walls 5 and 5 to extend over the entire length of the main body of the absorbent article 1 (i.e., from end edge of the front portion 3, through the intermediate portion 2, to the end edge of the rear portion 4). Each leakage preventing wall 5 is formed of a sheet such as non-woven fabric, which is joined to the surface member 10 at a position inside of the leakage preventing wall 5, and is extended outwardly of the leakage preventing wall 5 and joined to the backing sheet 7 with a hot melt adhesive or the like, at a flap portion 6 outside of the leakage preventing wall 5.

In the embodiment shown, the surface member 10 is provided over the entire length of the main body of the absorbent article 1, but should not be limited thereto. For example, the surface member 10 may be provided only at the intermediate portion 2, especially only at the center portion of the liquid-absorbing region where the absorbent core 8 is present.

The backing sheet 7 is impermeable to liquid, and is formed of a moisture permeable (breathable) resin film, a non-woven fabric or a laminate of a resin film and a non-woven fabric. The absorbent core 8 is formed of a mixture of crushed pulp and SAP (superabsorbent polymer) wrapped in liquid permeable paper, air laid pulp formed into a sheet form by binder process, absorbent paper, a non-woven fabric primarily consisted of hydrophilic fibers, or the like.

The aforementioned sheet forming the leakage preventing wall 5 (also forming the flap portion 6 together with the backing sheet 7) may be formed of a non-woven fabric, such as through-air bonded non-woven fabric, point bonded non-woven fabric, spun bonded non-woven fabric, spun laced non-woven fabric, melt blown non-woven fabric or air laid non-woven fabric, which is preferably hydrophobic or water repellent.

As shown in FIG. 3B, the surface member 10 is formed with an upper layer 10a appearing on a liquid-receiving side surface, and a lower layer 10b positioned adjacent to the absorbent core 8. The upper layer 10a and the lower layer 10b are formed of first continuous filaments 11a and second continuous filaments 11b, respectively. These individual continuous filaments 11a and 11b extend in the Y direction without any interruption. In other words, the individual continuous filaments 11a and 11b extend over the entire length of the surface member 10. Here, the continuous filaments 11a and 11b are crimped.

As described in detail hereinafter, the upper layer 10a is formed of a filament bundle (generally called as "tow"), in which the crimped continuous filaments 11a are bundled. Similarly, the lower layer 10b is also formed of a filament bundle (generally called as "tow"), in which the crimped continuous filaments 11b are bundled. These filament bundles (i.e., tows) are opened, spread into a predetermined width, and joined to each other to form the surface member 10. These continuous filaments 11a and 11b are occasionally referred to as tow filaments.

The continuous filaments 11a and 11b are made of heat-fusible, hydrophobic synthetic resin. For example, the continuous filaments 11a and 11b may be mono-fibers, such as those of PE (polyethylene), PP (polypropylene), PET (polyethylene terephthalate) or the like, conjugated synthetic fibers of core-sheath structure, such as those of PE/PET, PE/PP or the like, or conjugated synthetic fibers of side-by-side structure, such as those of PE/PET, PE/PP or the like. The continuous filaments 11a and 11b preferably contain inorganic filler for whitening, such as titanium oxide or the like, in the content of 0.5 to 10% by weight. By whitening process, the menstrual blood absorbed in the absorbent core 8 can be easily concealed from external view. The individual continuous filaments may have a circular or modified cross-section.

Crimping is provided for continuous filaments upon production by means of crimper, and number of crimp is increased by pre-heating calender or hot air treatment. In the alternative, through pre-heating calender, drawing and relaxing are repeated to cause strain in orientation of resin forming continuous filaments to cause crimp in coil form.

Opening of a bundle of crimped continuous filaments can be performed as following. While the bundle is transported between transporting rolls, tension force is applied in the direction along which the filaments extend, and then the tension force is released. These processes are repeated to separate individual continuous filaments from each other for opening. In the alternative, it is also possible to perform opening of the bundle by urging sliding plates onto the bundle from opposite sides. In this method, the bundle transported between transporting rolls is slidingly contacted with the sliding plates, and individual filaments are separated from each other by sliding contact force for opening. The latter method employing the sliding plates has been disclosed in commonly owned co-pending U.S. patent application for "METHOD AND APPARATUS FOR OPENING CONTINUOUS FILAMENTS" (claiming priority based on Japanese Patent Application No. 2000-265458). The disclosure of the above-identified commonly owned co-pending U.S. patent application is herein incorporated by reference. The bundle of continuous filaments thus opened has a small filament density and a large apparent width.

Furthermore, the opened filament bundle is spread (widened) in the width direction to have a uniform bulkiness and to have a width substantially matching with the width of the surface member 10 shown in FIG. 1.

As described above, the bundle of the continuous filaments 11a for forming the upper layer 10a and the bundle of the continuous filaments 11b for forming the lower layer 10b are opened and spread, respectively, and then stacked as shown in FIG. 3A. The upper layer 10a and the lower layer 10b thus stacked are clamped by welding rolls, at least one of which contains a pattern of protrusions for embossing on the peripheral surface, for forming fixing lines 12. At respective fixing lines 12, the continuous filaments 11a of the upper layer 10a and the continuous filaments 11b of the lower layer 10b are heat fused or welded by induction heating with ultrasonic wave to thereby form the layers 10a and 10b into a sheet.

In the embodiment shown in FIGS. 1 and 2, the individual fixing lines 12 extend across the surface member 10 in the X direction in the form of continuous line approximated to trigonometric curve. In the Y direction along which the individual continuous filaments 11a and 11b extend, the fixing lines 12 are spaced apart from each other by a given pitch P. The pitch P of the fixing lines 12 is in a range of 20 to 50 mm. However, fixing lines should not be limited to the shown wavy shape but may extend in various forms, for example, in the form of straight line or V-shaped line. It is also possible to provide a plurality of short fixing lines intermittently arranged at a given interval in the X direction, so long as consideration is given to prevention of falling out of filaments. Various alternation of the short fixing line patterns are disclosed in commonly owned co-pending U.S. patent application, for "ABSORBENT ARTICLE EMPLOYING SURFACE LAYER WITH CONTINUOUS FILAMENT AND MANUFACTURING PROCESS THEREOF" (claiming priority based on Japanese Patent Application No. 2000-265467). The disclosure of the above-identified commonly owned co-pending U.S. patent application will be herein incorporated by reference. Of course, it is possible to replace the short fixing lines with circular dot-shaped fixing portions or the like.

The surface member 10, which consists of the upper layer 10a and the lower layer 10a, has a total basis weight in a range of 5 to 100 g/m², and preferably in a range of 10 to 60 g/m². The upper layer 10a and the lower layer 10b preferably have the same basis weight, but may have different basis weights. Here, the filament weight ratio of the upper layer 10a to the lower layer 10b is in a range of 5:95 to 95:5, and preferably in a range of 30:70 to 70:30. In the surface member 10, in which the upper layer 10a and the lower layer 10b are combined, the average filament density is in a range 0.002 to 0.01 g/cm³.

The individual continuous filaments 11a and 11b of the respective upper and lower layers 10a and 10b have a fineness in a range of 1.1 to 20 dtex, and preferably in a range of 1.1 to 11 dtex.

In the individual continuous filaments 11a and 11b, number of crimp is in a range of 5 to 30 per inch, and preferably in a range of 15 to 30, and crimp modulus of elasticity is preferably greater than or equal to 70%.

Number of crimp is based on JIS L-1015 and crimp modulus of elasticity is based on JIS L-1074. In case of the filament of a fineness less than 5.5 dtex, an initial load of 0.49 mN is applied in pulling direction, and in case of the filament of a fineness greater than or equal to 5.5 dtex, an initial load of 0.98 mN is applied in pulling direction. Number of crimp referred to is number of threads (peaks) per 1 inch (25 mm) when the initial load is applied.

On the other hand, the crimp modulus of elasticity is expressed by:

$\{(b-c)/(b-a)\} \times 100(\%)$ wherein a is a length of filament when the initial load is applied, b is a length when the crimp is stretched by applying a tension force of 4.9 mN per 1.1 dtex for 30 seconds, and c is a length as applied the initial load again after 2 minutes from releasing the tension force.

In the surface member 10, the continuous filaments 11a of the upper layer 10a and the continuous filaments 11b of the lower layer 10b have different hydrophilicities with each other, such that the lower layer 10b has a higher hydrophilicity than that of the upper layer 10a. In addition, the upper layer 10a and the lower layer 10b have different filament densities with each other, such that lower layer 10b has a higher filament density than that of the upper layer 10a. However, the upper layer 10a may have a higher filament density than that of the lower layer 10b, if desired.

Here, a difference in hydrophilicity represents a difference in interfacial chemical nature on the filament surface, and hydrophilicity becomes higher at lower contact angle of water, in case of hydrophobic filament.

As set forth, the continuous filaments 11a of the upper layer 10a and the continuous filaments 11b of the lower layer 10b are hydrophobic filaments, such as core-sheath type conjugated fiber of PE/PP or PE/PET. In the case where these hydrophobic continuous filaments 11a and 11b are both treated to be hydrophilic by applying a hydrophilic oil solution onto the surfaces of the continuous filaments, a difference in hydrophilicity can be provided by using hydrophilic oil solutions having different durabilities against liquid.

For example, onto the continuous filaments 11a of the upper layer 10a, applied is an initial hydrophilic oil solution, namely a hydrophilic oil solution which can relatively easily drop off as contacting with water or other liquid. This kind of initial hydrophilic oil solution may be PEG modified polyester, polyoxyethylene alkyl sulfate, alkyl phosphoric ester K salt, polyoxyethylene alkyl ester, alkylsulfonate Na salt and so forth. On the other hand, onto the continuous filaments 11b of the lower layer 10b, applied is a durable hydrophilic oil solution which is difficult to drop off by water or other liquid in comparison with the initial hydrophilic oil solution. The durable hydrophilic oil solution may be polyether ester, ether nonion, polyether modified silicon, sulfo succinate, polyoxyethylene amide ether, alkyl imidazoline type cation, polyglycerol polyester and so forth. With the hydrophilic oil solutions being thus selected to make the durability of hydrophilic oil solution against liquid higher in the lower layer 10b than in the upper layer 10a, the lower layer 10b is permitted to have a higher hydrophilicity than that of the upper layer 10a.

In an alternative, a difference in hydrophilicity may be provided by applying the same hydrophilic oil solution onto both the continuous filaments 11a and 11b of the upper and lower layers 10a and 10b, such that an application amount of hydrophilic oil solution per unit fineness (1 dtex) of continuous filaments is greater in the lower layer 10b than in the upper layer 10a.

In another alternative, a difference in hydrophilicity may also be provided such that only the hydrophobic continuous filaments 11b of the lower layer 10b are treated to be hydrophilic by applying a hydrophilic oil solution onto the filaments or by kneading a hydrophilic oil solution into the filaments, while the hydrophobic continuous filaments 11a of the upper layer 10a are not processed by the hydrophilic treatment.

Moreover, it is also possible to provide a difference in hydrophilicity by utilizing hydrophilic fibers. Hydrophilic fibers can draw moisture by hydrophilic group on the surface thereof. Here, examples of the hydrophilic fibers include hydrophilic continuous filaments, such as those of cellulose acetate, and hydrophilic short fibers, such as natural cellulose fibers. The hydrophilic continuous filaments, such as those of cellulose acetate, may be mixed with the hydrophobic continuous filaments 11b to form the lower layer 10b, while the upper layer 10a being formed only of the hydrophobic continuous filaments 11a. Alternatively, the hydrophilic continuous filaments may be mixed with the hydrophobic continuous filaments 11a and 11b, respectively, to form the upper layer 10a and lower layer 10b, in which a content of the hydrophilic continuous filaments is higher in the lower layer 10b. Of course, it is possible to prepare the lower layer 10b only of the hydrophilic continuous filaments, if desired. On the other hand, the hydrophilic short fibers, such as natural cellulose fibers, may be bonded to the hydrophobic continuous filaments 11b of the lower layer 10b with an adhesive or the like, for enhancing hydrophilicity of the lower layer 10b.

Next, a difference in density can be adjusted by varying the fineness of the continuous filaments. For example, by making the fineness of the continuous filaments 11b of the lower layer 10b smaller that of the continuous filaments 11a of the upper layer 10a, the density of the lower layer 10b can be made higher than the density of the upper layer 10a.

Alternatively, a difference in density may also be provided between the upper and lower layers 10a and 10b by varying number of crimp of the continuous filaments and/or by varying crimp modulus of elasticity. For example, by providing greater number of crimp for the continuous filaments 11b of the lower layer 10b than that of the continuous filaments 11a of the upper layer 10a, the density of the lower layer 10b can be made higher. On the other hand, by making the crimp modulus of elasticity of the continuous filaments 11b of the lower layer 10b higher than the crimp modulus of elasticity of the continuous filaments 11a of upper layer 10a, the density of the lower layer 10b can be made lower.

Here, it is preferred to provide a difference in number of crimp greater than or equal to 10 per inch between the upper layer 10a and the lower layer 10b, and it is also preferred to provide a difference in crimp modulus of elasticity in the extent greater than or equal to 10% between the upper layer 10a and the lower layer 10b. Also, a difference in density between the upper layer 10a and the lower layer 10b is preferably in the extent greater than or equal to 0.003 g/cm³.

On the other hand, as shown in FIG. 4, the surface member 10 may further comprise a liquid permeable non-woven fabric sheet 15 formed of hydrophilic fibers. In this construction, the continuous filaments 11b of the lower layer 10b and the continuous filaments 11a of the upper layer 10a are stacked on the non-woven fabric sheet 15, and the non-woven fabric sheet 15, the lower layer 10b and the upper layer 10a are fixed together at the fixing lines 12.

Also, it is possible to provide one or more intermediate layers of continuous filaments between the upper layer 10a and the lower layer 10b. In other words, the surface member 10 may be formed with three or more layers of mutually different continuous filaments. In this case, it is preferred to gradually increase hydrophilicity toward the lower layer.

In the absorbent article 1 as has been described above, the surface member 10 as a portion to contact the skin of a wearer, is formed of the continuous filaments. Therefore, no fiber end appears on the surface to thereby provide smooth contact feeling to the skin. Furthermore, since the continuous filaments can move independently to follow movement of the skin, the surface member 10 becomes less irritative to the skin. Also, the surface member 10 is so bulky as to provide superior cushioning characteristics.

Furthermore, in the surface member 10 composed of the upper layer 10a and the lower layer 10b, the lower layer 10b has a higher hydrophilicity. Therefore, the liquid applied on the surface of the surface member 10 is drawn to the lower layer 10b and thus supplied to the absorbent core 8. This results in reducing an amount of residual liquid in the upper layer 10a. If the density of the lower layer 10b is made higher than that of the upper layer 10a, the body fluid can be drawn to the lower layer 10b by capillary effect. In this case, too, an amount of residual liquid in the upper layer 10a can be reduced. Furthermore, since the upper layer 10a serves for preventing the liquid from flowing back from the absorbent core 8, the liquid absorbed in the absorbent core 8 hardly flows back toward the skin of a wearer (i.e., rewet hardly occurs).

If the density of the upper layer 10a is made higher than the density of the lower layer 10b, on the other hand, rewet-preventing property can be enhanced by the high density of the continuous filaments 11a of the upper layer 10a.

On the other hand, since the individual continuous filaments 11a and 11b extend in the longitudinal direction (Y direction) of the absorbent article 1, the liquid applied to the surface member 10 is easily guided in the longitudinal direction to thereby reduce or eliminate side leakage in the width direction (X direction). Furthermore, since the continuous filaments 11a and 11b are fixed at the fixing lines 12 spaced apart from each other by the given pitch P in the longitudinal direction, spreading or propagation of the liquid in the longitudinal direction in the surface member 10 can be restricted. Thus, the liquid can be easily guided to the absorbent core 8.

Since the upper layer 10a and the lower layer 10b having different hydrophilicities and densities can be formed by simply stacking and fixing opened tows of continuous filaments, manufacturing process becomes quite simple. Furthermore, since no adhesive is disposed between the upper and lower layers 10a and 10b for fixing them at the fixing lines 12, migration of liquid toward the absorbent core may not be interfered by adhesive.

As set forth above, in the present invention, the surface member of the absorbent article may have good liquid permeability with prevention of flowing back of the liquid. Moreover, the surface member may provide soft contact feeling on the skin of a wearer and superior cushioning characteristics. Still moreover, the surface member having a difference in hydrophilicity can be easily manufactured with simple process of stacking two opened bundles of continuous filaments.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

For instance, while the surface member is formed over entire surface of at least the central portion of the absorbent article, it is also possible to form the surface member into a plurality of strips arranged in parallel in spaced apart relationship. Such construction has been disclosed in commonly owned co-pending U.S. patent application, for "ABSORBENT ARTICLE HAVING FIBROUS LAYER ON SURFACE" (claiming priority based on Japanese Patent Application No. 2000-265476). The disclosure of the above-identified commonly owned co-pending U.S. patent application is herein incorporated by reference.

What is claimed is:

1. An absorbent article comprising:

a liquid permeable surface member;

a backing sheet; and an absorbent layer interposed between said surface member and said backing sheet, said surface member having at least two layers including an upper layer located at a liquid-receiving side surface and a lower layer located adjacent to said absorbent layer, said upper layer being formed of first continuous filaments, said lower layer being formed of second continuous filaments, said first and second continuous filaments individually extending over an entire length of said surface member, wherein said first continuous filaments are prepared by applying at least one compound selected from the group consisting of PEG modified polyester, polyoxyethylene alkyl sulfate, alkyl phosphoric ester K salt, polyoxyethylene alkyl ester, and alkylsulfonate Na salt on surfaces of hydrophobic filaments, and said second continuous filaments are prepared by applying at least one compound selected from the group consisting of polyether ester, ether nonion, polyether modified silicon, sulfo succinate, polyoxyethylene amide ether, alkyl imidazoline type cation, and polyglycerol polyester on surfaces of hydrophobic filaments so that a hydrophilicity of said lower layer is higher than a hydrophilicity of said upper layer.

* * * * *